United States Patent [19]

Mora

[11] Patent Number: 4,631,293

[45] Date of Patent: Dec. 23, 1986

[54] (−) CAMPHOLENIC ACID ESTER OF SALICYLIC ACID AND PHARMACEUTICALLY ACCEPTABLE SALTS THEREOF HAVING MUCOSECRETOLYTIC, ANTI-INFLAMMATORY, ANALGESIC, AND ANTIPYRETIC ACTIVITY

[75] Inventor: Camillo C. Mora, Piacenza, Italy

[73] Assignee: Camillo Corvi S.p.A., Italy

[21] Appl. No.: 734,067

[22] Filed: May 15, 1985

[30] Foreign Application Priority Data

Jun. 26, 1984 [IT] Italy ................................. 21608/84

[51] Int. Cl.$^4$ ...................... C07C 69/74; A61K 31/235
[52] U.S. Cl. ...................................... 514/530; 560/122
[58] Field of Search ......................... 560/122; 514/530

[56] References Cited

U.S. PATENT DOCUMENTS

| | | | |
|---|---|---|---|
| 2,561,193 | 7/1951 | Fry | 560/122 |
| 2,835,697 | 5/1958 | Murray | 560/122 |
| 3,519,678 | 7/1970 | Farrington | 560/122 X |
| 3,673,237 | 6/1972 | Janiak | 560/122 |

*Primary Examiner*—Natalie Trousof
*Assistant Examiner*—Patricia M. Scott
*Attorney, Agent, or Firm*—Ostrolenk, Faber, Gerb & Soffen

[57] ABSTRACT

A novel salicylic acid ester is described, which may be combined with inorganic or organic bases to give pharmaceutically acceptable salts. Such an ester is obtained by reaction of (−) campholenic acid chloride, as prepared by a well known technique, with salicylic acid.

There are, further, described pharmaceutical compositions having mucosecretolytic, anti-inflammatory, analgesic, antipyretic activity, which contain the novel ester or the salts thereof.

10 Claims, No Drawings

(−) CAMPHOLENIC ACID ESTER OF SALICYLIC ACID AND PHARMACEUTICALLY ACCEPTABLE SALTS THEREOF HAVING MUCOSECRETOLYTIC, ANTI-INFLAMMATORY, ANALGESIC, AND ANTIPYRETIC ACTIVITY

DESCRIPTION OF THE INVENTION

The object of the present invention is the (−) campholenic acid ester of salicylic acid, having the following formula:

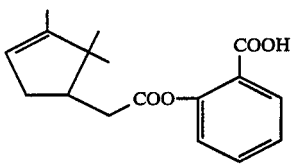

(I)

Code 1473 $C_{17}H_{20}O_4$ mol.wt 288.35 2-(2,2,3-trimethyl-3-cyclopentene-1-acetoxy)benzoic acid.

It has been found, unexpectedly, that the ester of formula (I) combines with anti-inflammatory, analgesic and antipyretic activity, a marked mucolytic activity on the bronchial secretion.

In the therapeutic practice, the difunctional molecule of the present invention is suggested as a mucosecretolytic, anti-inflammatory, analgesic, antipyretic drug for the treatment of respiratory bronchopneumonic diseases, associated with inflammatory symptoms.

An object of this invention is also to provide a process for the preparation of the novel bifunctional molecule, which consists of preparing the chloride of (−) campholenic acid, (−) 2-(2,2,3-trimethyl-3-cyclopentene)-1-acetic acid by reacting with oxalyl chloride $C_2Cl_2O_2$ (see Merck Index, Tenth Ed. N. 6786) and thereafter condensing with salicylic acid.

The reaction is suitably carried out in an aprotic solvent, such as ethyl ether, tetrahydrofuran, dioxane, and anhydrous methylene chloride, in the presence of an acid acceptor. As such, organic bases, such as tertiary amines of the pyridine or triethylamine type, are preferably used.

The reaction may be carried out within a temperature range from 10° to 100° C., preferably from 20° to 80° C.

The preparation is completed by the usual processes of neutralization, extraction, washing, dry concentration and chromatography purification.

The present invention will now be illustrated by the following examples, which, however, shall not limit the same.

SYNTHESIS SCHEME OF CO/1473

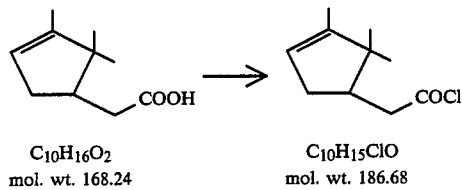

$C_{10}H_{16}O_2$
mol. wt. 168.24

$C_{10}H_{15}ClO$
mol. wt. 186.68

-continued
SYNTHESIS SCHEME OF CO/1473

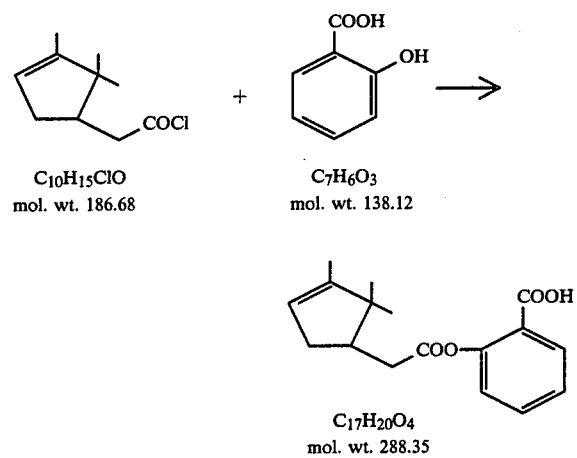

$C_{10}H_{15}ClO$
mol. wt. 186.68

$C_7H_6O_3$
mol. wt. 138.12

$C_{17}H_{20}O_4$
mol. wt. 288.35

EXAMPLE 1

SYNTHESIS OF CO/1473

To a solution of 34 g of (−) campholenic acid in 500 ml of methylene chloride, 52 ml of oxalyl chloride and 0.5 ml of dimethylformamide are added. The mixture is left under stirring at room temperature during 3 hours and then is evaporated to dryness. The (−) campholenic acid chloride, so obtained, is dissolved into 100 ml of tetrahydrofuran and it is added slowly to a previously prepared solution of 27.9 g of salicyclic acid and 25.6 ml of trimethylchlorosilane in 150 ml of pyridine.

The resulting mixture is left under stirring for 12 hours, then it is poured into 20% sulphuric acid and is extracted with ethyl acetate. The organic phases, having been combined, are washed with water and dried, at first in a desiccator and thereafter by evaporation.

The raw product (55 g) is chromatographed on silica gel, by eluting with 1:1 cyclohexane/ethyl acetate. There are so obtained 46 g (80%) of a white crystalline product, m.p. 93°–95° C.

Preparation of pharmaceutically acceptable salts

Product (I) of the present invention can be converted, by per se known methods, to the corresponding pharmaceutically acceptable salts, in particular to the inorganic sodium and potassium salts thereof, which may be obtained by neutralization by means of the respective bicarbonates in aqueous or hydrocalcoholic media at such conditions as to avoid hydrolvsis of ester (I) and to aid the precipitation of the pharmaceutically acceptable salt.

Pharmaceutically acceptable organic salts can be obtained by combining ester (I) with such aminoacids as lysine or arginine in an alcoholic (methanol or ethanol) medium or by evaporating to dryness or by crystallisation.

The DL-lysine salt as obtained from isopropanol is mentioned in Example 2.

EXAMPLE 2

DL-lysine salt of CO/1473

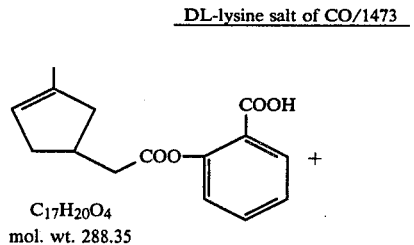

C$_{17}$H$_{20}$O$_4$
mol. wt. 288.35

H$_2$NCH$_2$(CH$_2$)$_3$CHCOO$^\ominus$
                 |
                 NH$_3^\oplus$ C$_6$H$_{14}$N$_2$O$_2$
mol. wt. 146.19

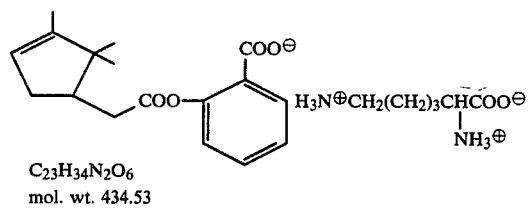

C$_{23}$H$_{34}$N$_2$O$_6$
mol. wt. 434.53

To a solution of 30 g (0.104 mole) of the compound of this invention, in 600 ml of isopropanol, 14.7 g (0.1 mole) of DL-lysine as a 50% aqueous solution are added under vigorous stirring. The reaction mixture is concentrated under vacuum to a volume of about 150 ml and is left under stirring for three hours. It is then filtered under vacuum, to obtain 40 g (92%) of white crystalline product with m.p. 130°–132° C.

CO/1473 C$_{17}$H$_{20}$O$_4$
Analytical data
1. Elemental analysis

| Theory: | C = 70.81% | H = 6.99% | O = 22.19% |
|---|---|---|---|
| Found | C = 70.98% | H = 7.18% | |
| | C = 70.78% | H = 7.20% | |
| | C = 70.91% | H = 6.93% | |

2. I.R. spectrum (nujol dispersion; cm$^{-1}$)

| 2700 24500 | υ OH acid |
| 1772 | υ C=O ester |
| 1700 | υ C=O acid |
| 1608 and 1487 | phenyl nucleus |
| 1410,1269, | characteristic bands |
| 1210,1130, | |
| 789 | |

3. N.M.R. spectrum (CDCl$_3$ solvent; T.M.S. reference; δ p.p.m.):

| 8.2 ÷ 7.73 ÷ 7 | c.a. (4H; aromatic hydrogens) |
| 5.25 centre, | c.a. (1H; =C$\underline{H}$) |
| 2.90 ÷ 1.73 | c.a. (5H; C$\underline{H}_2$—C$\underline{H}$—C$\underline{H}_2$—CO) |
| 1.62 | b.s. (3H; C$\underline{H}_3$=) |
| 1.07 and 0.87 | 2 s. (6H; gem. C$\underline{H}_3$) | c.a. = complex absorption
b.s. = broadened singlet
2 s = 2 singlets
T.M.S. = tetramethylsilane MS (quadrupole): electronic impact, direct connection 80 eV, 80 m.A.; m/z):
288(M+, 1%); 207(3%); 181(1%); 168(11%); 153(23%); 151(6%); 150(7%); 138(52%); 135(9%); 123(4%); 121(29%); 120(base peak); 111(10%); 109(35%); 108(72%); 107(51%); 93(47%); 92(73%); 91(20%); 81(16%); 64(28%).

CO/1473, Lysine salt
C$_{23}$H$_{34}$N$_2$O$_6$
mol.wt. 434.538
I.R. (nujol dispersion; cm$^{-1}$):

| 2800 ÷ 2000 | "ammonium bands" |
| 1740 | υ c = or ester |
| 1660 | |
| 1610 | υ s and υ as COO$^\ominus$; phenyl nucleus; |
| 1588 | δ as and δ s NH$_3^\oplus$ |
| 1552 | |
| 1200;1152;1140;858;779 characteristic bands | |

N.M.R. (D$_2$O solvent; D.S.S. reference; δ p.p.m.):

| 7.9 ÷ 7.1 | c.a. (4H; aromatic hydrogens) |
| 5.42 | centre; c.a. (1H; =CH) |
| 3.75 | t. (1H; —CH$_2$—C$\underline{H}$—NH$_3^\oplus$) |
| 3.03 | t. (2H; H$_3$N$^\oplus$—C$\underline{H}_2$—CH$_2$) |
| 2.9 ÷ 1.2 | c.a. (11H; C$\underline{H}_2$—C$\underline{H}$—C$\underline{H}_2$ and CH$_2$—(CH$_2$)$_3$—CH) |
| 1.67 | b.s. (3H; CH$_3$—C=) |
| 1.07 and 0.87 | 2 s. (6H; gem CH$_3$) | c.a. = complex absorption
b.s. = broadened singlet
t. = triplet
2s. = 2 singlets
D.S.S. = 3-(trimethylsilyl)-propane sulphonic acid, sodium salt.

Toxicity

Method for studying the lethal dose 50(LD$_{50}$) in the mouse after a single administration.

Groups of 10 Swiss albine, female, adult (20–22 g of body weight) mice, fasting from the evening preceding the test, are treated orally with various doses of the test drug suspended in hydroxyethylcellulose (0.50% weight/volume).

Thereafter, the animals are fed again.

LD$_{50}$ is calculated by the method of Litchfield J. T. and Wilcoxon F. (J. Pharmacol. 96, 99–113, 1949) by utilizing the mortality data as obtained on the 14th day after the test drug administration.

TABLE No. 1
TOXICITY

| Compound | $LD_{50}$ in mg/kg os. |
|---|---|
| CO/1473 (compound of the present invention) | 913 |
| acetylsalicylic acid | 1100* |

*literature datum, see Hart E R - J. Pharm. Exp. Ther.-89 205,1947.

The results reported in Table 1 prove a low acute toxicity of CO/1473 in the mouse comparable that the one of acetylsalicylic acid.

BRONCHOSECRETAGOGUE ACTIVITY

Method of quantitative evaluation of the bronchial secretion of rabbit according to Scuri R. et al. Boll. Chim. Farm. 119,181–7, 1980.

Adult male brown rabbits (2.8–3.5 kg of body weight) are employed, to which a T shaped tracheal cannula, by surgical operation, as described in the mentioned bibliographic reference, is applied.

To the cannula, a container for periodical collection of the bronchial secretion is applied.

The study of mucoproduction, started at the fourth day after the operation, is divided into two periods, each of 4 hours, for collecting and measuring the mucus secreted. The action of the drug under examination, is tested by administering the same orally at the begining of the second mucus collection period and evaluating the percent increase of mucus production (as measured gravimetrically in the second period in comparison with the first period).

TABLE 2
BRONCHOSECRETAGOGUE ACTIVITY

| Compound | $ED_{50}$ in mg/kg os. |
|---|---|
| CO/1473 | 60 |
| acetylsalicylic acid | inactive |

From the data reported in Table 2, one can deduce that only the compound of this invention has bronchosecretagogue activity in the rabbit.

ANTI-INFLAMMATORY/ANTI-OEDEMIGENOUS ACTIVITY

Method of carrageenin induced oedema according to Winter C. A. et al—Proc. Soc. Exp. Biol. Med. 111, 544–7, 1962.

Female albine Wistar rats (120–160 g of body weight) are utilized.

The drug under test is administered orally one hour before injection into the right hind paw of a carrageenin water suspension (1% volume injected ml 0.05).

The volume of the injected paw is recorded simultaneously with the carrageenin injection and after three hours from the same, by means of a plethysmometer (U. Basile, mod. 7150-Comerio, Varese).

ANTI-INFLAMMATORY/ANTI-EXUDATIVE ACTIVITY

Method of the quantitative evaluation of the pleural exudate of a rat according to Vinegar E. et al.-Proc. Soc. Exp. Biol. Med. 143, 711–4, 1973.

Female albine Wistar rats (average weight 160 g), fasting from the evening preceding the test, are used.

The experimental pleuritis is induced by injecting into the pleural cavity, under ethereal anesthesia, 0.15 ml of a 1% carrageenin solution (Prodotti Gianni-Milano).

The test drug is administered orally, half an hour before the carrageenin.

Six hours after the carrageenin injection, the animals are sacrificed and volumetric measurement of the pleural exudate, as withdrawn by a syringe, is performed.

The effect of the test drug is proved by the decrease in the exudate volume in comparison with the rats which have not received the drug (controls).

TABLE No. 3
ANTI-INFLAMMATORY ACTIVITY

| Compound | Anti-oedemigenous activity $ED_{40}$ in mg/kg os. | Anti-exudative activity $ED_{50}$ in mg/kg os. |
|---|---|---|
| CO/1473 | 400 | 320 |
| acetylsalicylic acid | 400 | 215 |

In Table 3, the results of the tests performed in order to evaluate the anti-inflammatory activity of the compound of the invention, in comparison with acetylsalicylic acid, in the rat, are reported.

Both the pharmacological tests, in fact, are broadly utilized to investigate such activity, particularly the anti-exudative activity test, in order to measure the drug efficiency against inflammations of the respiratory apparatus. In both tests, CO/1473 proves to be quite active and, in comparison with acetyl-salicylic acid, it shows superior in the first test, slightly inferior in the second.

ANALGESIC ACTIVITY

Phenylquinone method according to Hendershot L. C., Forsaith J.-J. Pharmacol., 125,237, 1959.

Female Swiss albine mice (20–25 g), fasting for 2 hours, are utilized.

The test drug is administered orally 30 minutes before the endoperitoneal injection of phenylquinone (0.08 mg/mouse).

The characteristic abdominal contractions are counted individually during a 20 minutes period.

TABLE No. 4
ANALGESIC ACTIVITY

| Compound | $ED_{50}$ in mg/kg os. |
|---|---|
| CO/1473 | 52 |
| acetylsalicylic acid | 70 |

The data as reported in Table 4 prove that both the compounds are endowed with a good analgesic activity in the mouse and that CO/1473 is slightly more active than acetylsalicylic acid.

ANTIPYRETIC ACTIVITY

Method of yeast induced pyrexia in the rat.

Female Wistar albine rats, weighing 100–140 g, are utilized. The animals having a basal rectal temperature from 36° to 37° C. are selected.

The testing substances are administered orally simultaneously with the pyretic agent (dry brewers' yeast suspended in water at the 20% concentration, administered volume 15 ml/kg, subcutaneously) to groups of 5 animals per dose.

After 4, 5, 6, 7 and 24 hours from the treatment, the rectal temperature of the animals is recorded by an Ellab RM6 probe, connected to an Ellab-mod. TE-3 thermometer.

The activity of the drugs is evaluated by utilizing a Temperature Index, which is given by the algebraic sum of the differences in the rectal temperature between the measure values at different times and the basal value;

TABLE 5

| ANTIPYRETIC ACTIVITY | |
|---|---|
| Compound | $ED_{50}$ in mg/kg os. |
| CO/1473 | 400 |
| acetylsalicylic acid | 157 |

Table 5 shows that CO/1473 has an interesting antipyretic activity in the rat, though lower than the one of acetylsalicylic acid.

GASTRIC TOLERABILITY

Method of gastric ulcerogenesys by repeated drug administrations.

Fed female Wistar albine rats (140–160 g of initial body weight) are used.

The drug under test is administered orally, daily, for five days. At the end of the test the stomach of the rats is withdrawn, it is dissected along the lesser curvature, washed and observed in order to disclose the presence of either gastric lesions or manifest submucosa hemorrhages.

The "ulcerogenic dose 50" ($UD_{50}$) is defined as the daily dose able to induce lesions or hemorrhages in 50% of the animals treated.

TABLE No. 6

| GASTRIC TOLERABILITY | | |
|---|---|---|
| Compound | Dose used in mg/kg os. | Notes |
| CO/1473 | 800 | max dose used for the test. |
| acetylsalicylic acid | 48 | $UD_{50}$ in Arrigono-Martelli - Meth. Find. Exp. Clin. Pharmacol. 1, 157, 1979. |

The compound of the invention does not show any gastro-damaging effect in the rat up to the maximum dose of 800 mg/kg os/die for 5 days.

The acetylsalicylic acid, on the contrary, shows gastro-damaging effect already at a dose 16 times lower than that of CO/1473. This proves the very good gastric tolerability of the compound of the invention.

As regards the activity developed by the compound of formula (I) of the invention as well as by the pharmaceutically acceptable salts thereof, i.e. the mucosecretolyic, anti-inflammatory, analgesic and antipyretic activity, the present invention further provides pharmaceutical compositions containing the compound of formula (I) of this invention or its pharmaceutically acceptable salts in unit dose.

The pharmaceutical forms containing said active element are preferably those for oral or rectal administration, and particularly: capsules, tablets, syrup, granular form in sachets, and suppositories.

As excipients there may be employed, for oral pharmaceutical forms: starch, lactose, microgranular cellulose, polyvinylpyrrolidone, sorbitol, and more generally, diluting, binding, lubricating, aromatizing, flavour masking and edulcorating agents.

For the suppository form, as excipients, triglycerides of saturated fatty acids, lecithin and phospholipids commonly used in the pharmaceutical industry are employed.

I claim:

1. A (−) campholenic acid ester of salicylic acid, having the formula:

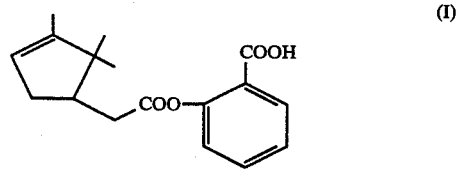

(I)

2. A pharmaceutically acceptable salt of the compound of formula (I) of claim 1.

3. The sodium salt of the compound of formula (I) of claim 1.

4. The potassium salt of the compound of formula (I) of claim 1.

5. The lysine salt of the compound of formula (I) of claim 1.

6. The arginine salt of the compound of formula (I) of claim 1.

7. A pharmaceutical composition having mucosecretolytic, anti-inflammatory, analgesic and antipyretic activity, characterized in that it contains, as an active ingredient an effective therapeutic amount of the compound of formula (I) of claim 1, together with at least one pharmaceutically acceptable vehicle.

8. A pharmaceutical composition having mucosecretolytic, anti-inflammatory, analgesic and antipyretic activity, characterized in that it contains, as an active ingredient an effective therapeutic amount of a pharmaceutically acceptable salt of the compound of the formula (I) of claim 1, together with at least one pharmaceutically acceptable vehicle.

9. A method of imparting mucosecretolytic, anti-inflammatory, analgesic and antipyretic activity in a host in need thereof which comprises administering to the host an effective therapeutic amount of the compound of formula (I) of claim 1 or a pharmaceutically acceptable salt thereof.

10. The method of claim 9 wherein said compound or pharmaceutically acceptable salt thereof is administered in combination with at least one pharmaceutically acceptable vehicle.

* * * * *